(12) United States Patent
Spazier et al.

(10) Patent No.: US 11,964,065 B2
(45) Date of Patent: Apr. 23, 2024

(54) ARRANGEMENT FOR IRRADIATING A SURFACE

(71) Applicant: Daimler AG, Stuttgart (DE)

(72) Inventors: Norbert Spazier, Bondorf (DE); Daniel Betz, Rottenburg-Seebronn (DE)

(73) Assignee: Daimler AG, Stuttgart (DE)

( * ) Notice: Subject to any disclaimer, the term of this patent is extended or adjusted under 35 U.S.C. 154(b) by 583 days.

(21) Appl. No.: 17/271,895

(22) PCT Filed: Aug. 13, 2019

(86) PCT No.: PCT/EP2019/071745
§ 371 (c)(1),
(2) Date: Feb. 26, 2021

(87) PCT Pub. No.: WO2020/043485
PCT Pub. Date: Mar. 5, 2020

(65) Prior Publication Data
US 2021/0187140 A1    Jun. 24, 2021

(30) Foreign Application Priority Data
Aug. 27, 2018  (DE) ................ 10 2018 006 769.7

(51) Int. Cl.
*A61L 2/10*   (2006.01)
*A61L 2/24*   (2006.01)
*B60S 1/64*   (2006.01)

(52) U.S. Cl.
CPC *A61L 2/10* (2013.01); *A61L 2/24* (2013.01); *B60S 1/64* (2013.01); *A61L 2202/11* (2013.01); *A61L 2202/14* (2013.01); *A61L 2202/25* (2013.01)

(58) Field of Classification Search
CPC .......... A61L 2/10; A61L 2/24; A61L 2202/11; A61L 2202/14; A61L 2202/25; A61L 2202/16; B60S 1/64
USPC ............................ 250/492.1, 453.11, 455.11
See application file for complete search history.

(56) References Cited

U.S. PATENT DOCUMENTS

| 4,816,145 A | 3/1989 | Goudy, Jr. |
| 5,837,207 A | 11/1998 | Summers |
| 5,973,331 A * | 10/1999 | Stevens ..................... F26B 3/28 |
| | | 250/492.1 |

(Continued)

FOREIGN PATENT DOCUMENTS

| CN | 203087354 U | 7/2013 |
| CN | 106237351 A | 12/2016 |

(Continued)

OTHER PUBLICATIONS

PCT/EP2019/071745, International Search Report dated Mar. 9, 2020 (Three (3) pages).

(Continued)

*Primary Examiner* — Jason L McCormack
(74) *Attorney, Agent, or Firm* — Crowell & Moring LLP

(57) ABSTRACT

An arrangement for irradiating a surface includes a radiation source configured to emit ultraviolet radiation, a reflector for directional radiation of the ultraviolet radiation onto the surface, and a control device. A dose of the ultraviolet radiation required for sterilizing the surface and/or a dose already administered is settable and/or determinable by the control device.

11 Claims, 8 Drawing Sheets

(56) References Cited

U.S. PATENT DOCUMENTS

| | | | |
|---|---|---|---|
| 10,131,273 B2 | 11/2018 | Salter et al. | |
| 2010/0044582 A1* | 2/2010 | Cooper | A61L 2/10 250/455.11 |
| 2011/0002821 A1* | 1/2011 | Hyde | A61L 2/07 422/292 |
| 2012/0248332 A1 | 10/2012 | Kreitenberg et al. | |
| 2016/0136314 A1* | 5/2016 | Kreitenberg | A61L 2/10 250/492.1 |

FOREIGN PATENT DOCUMENTS

| | | |
|---|---|---|
| DE | 1 196 598 B | 7/1965 |
| DE | 698 07 206 T2 | 4/2003 |
| DE | 10 2016 110 547 A1 | 12/2016 |
| DE | 10 2015 115 029 A1 | 4/2017 |
| DE | 10 2017 113 179 A1 | 12/2017 |
| EP | 2 668 964 A1 | 12/2013 |
| GB | 2527964 A | 1/2016 |
| JP | 2015-182792 A | 10/2015 |
| WO | WO 2013/116566 A1 | 8/2013 |
| WO | WO 2016/069701 A1 | 5/2016 |
| WO | WO 2017/204774 A1 | 11/2017 |
| WO | WO 2018/030987 A1 | 2/2018 |
| WO | WO 2019/139743 A1 | 7/2019 |

OTHER PUBLICATIONS

German-language German Office Action issued in German application No. 10 2018 006 769.7 dated Mar. 18, 2019 (Eight (8) pages).

Chinese Office Action issued in Chinese application No. 201980056395.8 dated Oct. 24, 2022, with partial English translation (Fifteen (15) pages).

Chinese Office Action issued in Chinese application No. 201980056395.8 dated Apr. 18, 2023, with English translation (Fourteen (14) pages).

Chinese Office Action issued in Chinese application No. 201980056395.8 dated Mar. 25, 2022, with partial English translation (Fifteen (15) pages).

\* cited by examiner

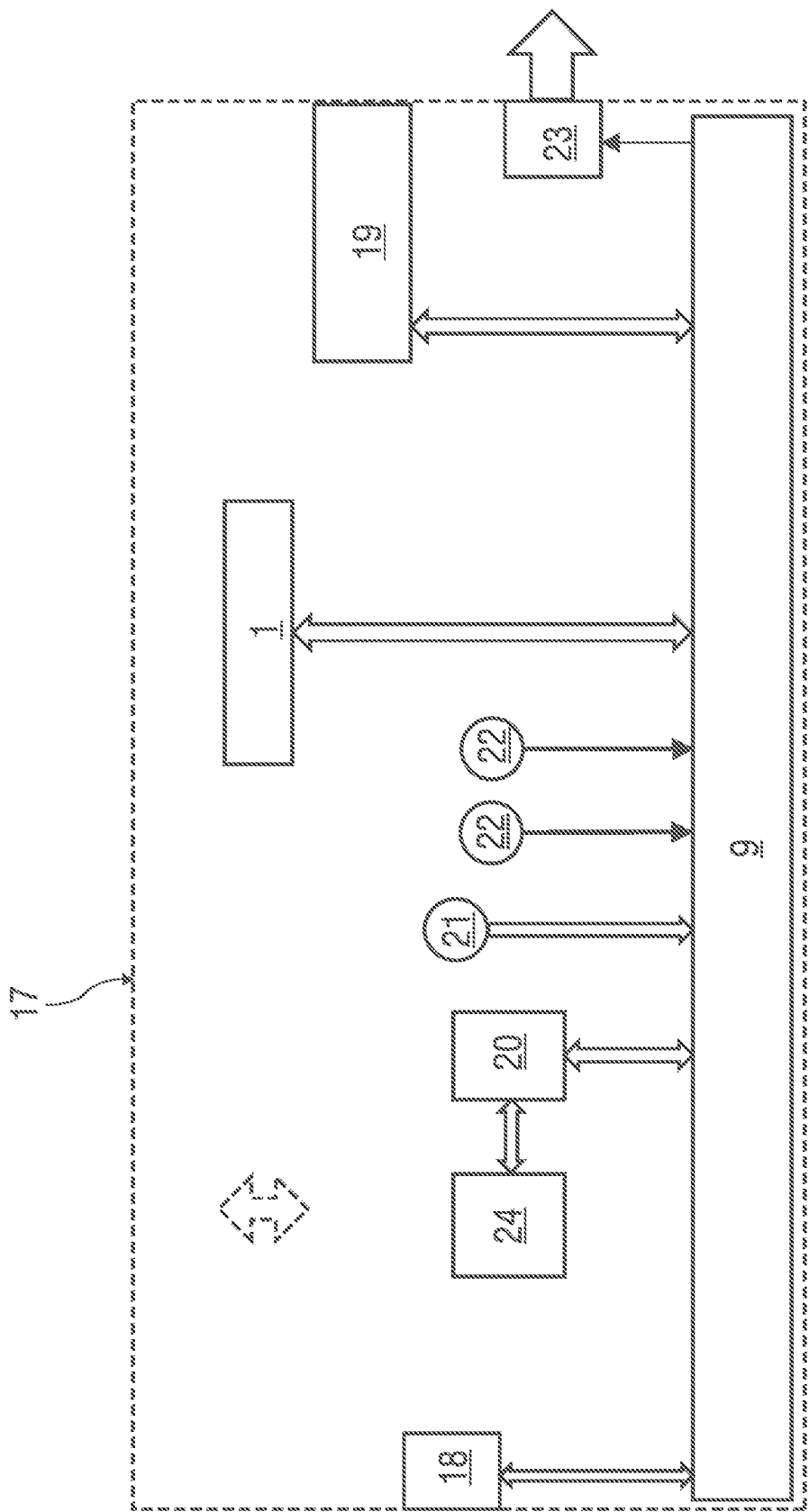

ARRANGEMENT FOR IRRADIATING A SURFACE

BACKGROUND AND SUMMARY OF THE INVENTION

The invention relates to an arrangement for irradiating a surface, in particular in a vehicle.

It is known to combat germs in biofilms, in particular pathogenic germs such as viruses, bacteria or fungi, for example, by means of ultraviolet radiation, in particular UV-C radiation. By way of example, a high radiation power over short periods of time or a low radiation power over longer periods of time can be used with the smallest possible distance from the surface to be irradiated.

A device having a flexible substrate and an ultraviolet radiation system is known from WO 2016/069701 A1. The ultraviolet radiation system can comprise at least one ultraviolet radiation source configured to emit ultraviolet radiation towards a surface to be disinfected, an ultraviolet transparent component for focusing the ultraviolet radiation, and a control system for controlling the at least one ultraviolet radiation source. The device can comprise a hand article such as a glove.

The object of the invention is to specify an improved arrangement for irradiating a surface.

An arrangement according to the invention for irradiating a surface comprises:

at least one radiation source which is designed to emit ultraviolet radiation, at least one reflector for the directed radiation of the ultraviolet radiation onto the surface, wherein a control device is provided, by means of which a dose of the ultraviolet radiation required for sterilizing a surface and/or already administered can be set and/or determined.

With the aid of the solution according to the invention, a lethal dose sufficient for the germs to be combatted is obtained on the surfaces to be irradiated.

The control can occur in such a way that sterilization occurs during empty journeys. In particular, the control can be carried out in such a way that only or especially those areas are sterilized where a high number of touches occur and/or which can be easily contaminated. The control can be designed to track which areas have already been sterilized. Based on radiation power and distance from the radiation source, an exposure duration can be calculated such that sterilization occurs safely and is terminated after sufficient exposure.

In one embodiment of the invention, at least one drive is provided for aligning the reflector.

The drive serves to position the radiation in order to improve the accessibility of surfaces to be irradiated, for example in vehicles, in particular vehicles intended for passenger transport such as passenger cars, buses, aircraft, autonomous vehicles, in particular vehicles for passenger transport with high density and changing persons such as taxis, rental vehicles and sharing vehicles. A further application is the use in vehicles provided for the transportation of food.

In one embodiment, the reflector is formed as a spherical section or semi-sphere on its outer surface.

In one embodiment, two drives are provided, each having a friction wheel that abuts an outer surface of the reflector, such that the reflector can be rotated around a first axis by means of one of the drives, and such that the reflector can be rotated around a second axis, which can be perpendicular to the first axis, by means of the other of the drives. Thus, grid-like traversing of an area by ultraviolet radiation emitted by the arrangement is possible.

In one embodiment, the reflector is formed on an inner side for the most uniform distribution of the ultraviolet radiation on the surface to be irradiated, for example as an elliptical paraboloid. In this case, drives in particular can be dispensed with, such that the arrangement is simpler and less expensive.

In one embodiment, the reflector is formed on an inner side for concentrating the ultraviolet radiation on a small area of the surface to be irradiated, for example by forming the inner side of the reflector as a free-form reflector comprising two or more hollow shapes which focus at least a major part of the radiation on a common focal point. In this way, smaller areas can be selectively sterilized in a shorter time.

In one embodiment, an optical system for directing the ultraviolet radiation is provided in an optical path of the ultraviolet radiation exiting the reflector, which may comprise one or more lenses, for example at least one quartz-glass lens, to improve the focusing of the radiation to concentrate the radiation power onto a smaller area. In particular, the optical system may include a scattering lens and a converging lens downstream of the scattering lens in the beam path.

In one embodiment, the control unit can be used to adapt the duration of exposure to the radiation to a varying radiation power resulting from the alignment by means of the drive and a distance between the reflector and the surface to be irradiated that varies as a result.

In one embodiment, the control unit is designed to traverse the surface in a grid-like manner such that all relevant areas are irradiated with a lethal dose sufficient for germs in biofilms, in particular pathogenic germs such as viruses, bacteria or fungi.

In one embodiment, the control unit is designed to store the dose already administered when irradiation is interrupted and to continue irradiation after the interruption until the intended dose is reached.

In one embodiment, a vehicle interior and at least one arrangement according to any one of the preceding claims for sterilizing at least one surface in the vehicle interior are provided in a vehicle.

In one embodiment, means are provided in the vehicle for generating a negative pressure or a vacuum in the vehicle interior during operation of the arrangement.

By way of example, the at least one arrangement is arranged in a roof area of the vehicle.

The efficiency of the radiation can be increased by generating a vacuum or negative pressure in the empty vehicle interior, since in this way, extinction and absorption of the radiation are reduced and suspended matter is removed. This more effective use of ultraviolet radiation improves hygiene and protects interior materials.

In one embodiment, means for detecting living beings, in particular persons, in the vehicle interior and/or at least one emergency stop button can be provided to ventilate the vehicle interior when living beings are detected or the emergency stop button is actuated.

The arrangement can comprise one or more radiation sources, for example LEDs and/or mercury vapor lamps, which bring about an optimal and highly efficient alignment of the emitted radiation through their optimal placement and using a reflector specially designed for this purpose. In particular, the radiation sources emit ultraviolet radiation, for example UV-C radiation.

The surface to be sterilized can be at least a portion of a vehicle seat, a center console, a dashboard, one or more controls on a dashboard, or a steering wheel.

A number of factors can influence the lethality of the pathogenic germs to be eliminated, such as a biofilm in which pathogenic germs can be located, as well as the material of the surface to be irradiated on which these germs and biofilms reside.

Porous materials and soiling, behind which pathogenic germs can be located, make it more difficult to kill pathogenic germs.

Another role in the colonization of pathogenic germs is played by the metabolism of the germ. Germs that prefer a moist environment in the presence of carbon are more likely to colonize sites other than interior surfaces. However, surfaces contaminated with viruses and bacteria can generally be high-level sites of infection. Various studies have shown which viruses and bacteria are most commonly found on interior surfaces.

However, by using a sufficiently large administered dose of radiation, these factors can be neglected. Therefore, doses that reliably kill viruses and bacteria are preferably administered.

For viruses and bacteria, UV-C radiation doses of 1500 µJ/cm2 to 8000 µJ/cm2 are sufficient in the most favorable cases; for pathogenic fungi and yeasts, doses of 120,000 µJ/cm2 are correspondingly sufficient. Since the radiation power at the effective site is known, it can be calculated in the control unit how long (time portion of the dose) the area to be irradiated must be irradiated in order to achieve a reduction of the germ load by, for example, 99.9 percent. Targeted irradiation is possible; after an interruption in irradiation, irradiation can be continued in an equally targeted manner.

Systems that scan the area to be irradiated and those which irradiate a fixed area from one or more reflectors are possible. It should be noted that irradiation is harmful to health and should therefore only take place in the absence of human and animal occupants, i.e., during empty journeys, when stationary/being charged overnight etc.

Taking into account the growth phases of the different bacterial populations, renewed sterilization is not necessary before at least 24 hours have elapsed. In addition, the frequency of journeys and the throughput of different people (shared cars) can also be taken into account in the calculation of the possible new contamination and the resulting need for renewed sterilization of the surfaces. By way of example, if the vehicle is charged overnight, there is no possibility of people or animals being in the vehicle. The system begins the sterilization process, for example with a scanning system.

If the sterilization process is interrupted, the system remembers the position and the administered dose and continues the sterilization at the same position after the interruption.

In a system with fixed reflectors, irradiation is resumed after an interruption until the intended dose is reached.

All the information required for this is known to the control system and is processed using an algorithm developed for this purpose. Sensors and actuators are processed or controlled accordingly.

The system does not need to know what kind of germs are involved. Instead, a dose can be administered that is sufficient for all typically occurring, known germs. However, the dose should only be so large that the material of the surfaces to be irradiated is protected.

The required doses are known or prescribed from other applications, for example, sterilization in food and water treatment.

Exemplary embodiments of the invention are explained in more detail below with reference to the drawings.

BRIEF DESCRIPTION OF THE DRAWINGS

FIG. 12 is a schematic view of a system for evacuating a vehicle interior.

DETAILED DESCRIPTION OF THE DRAWINGS

Figure 1:
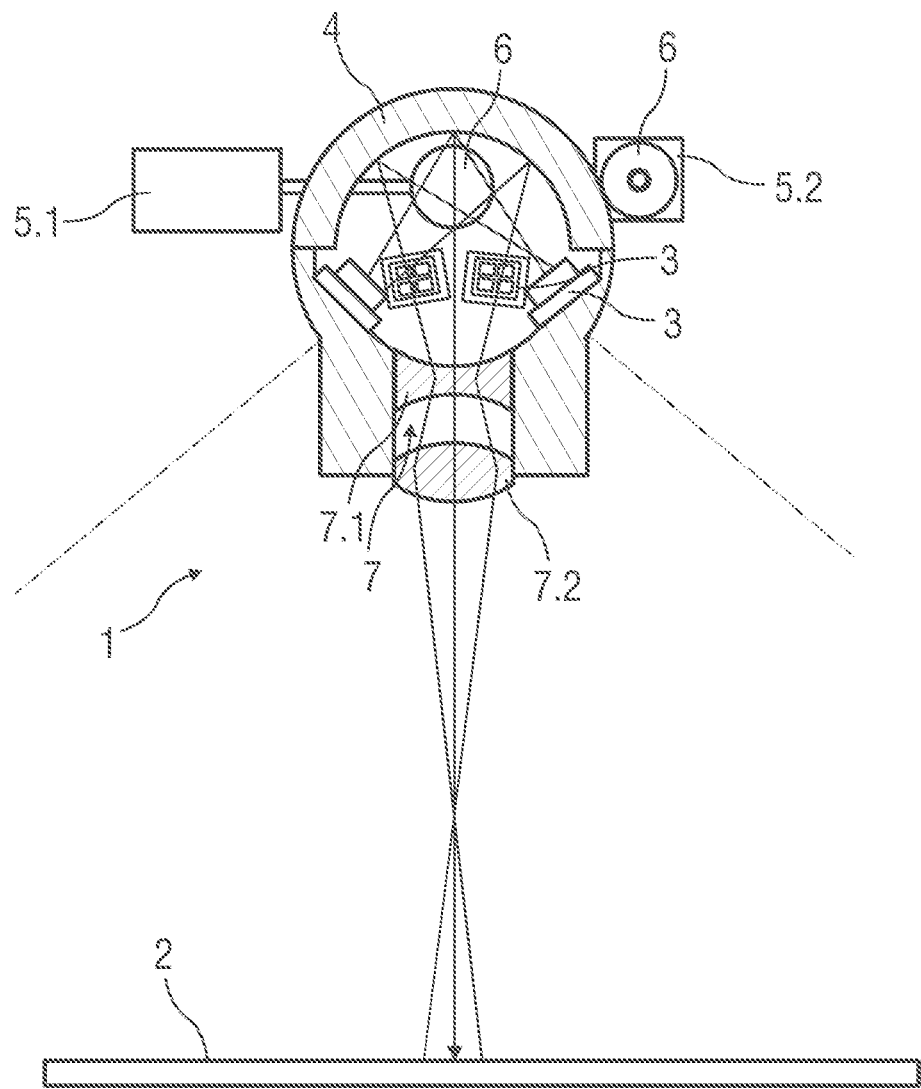
FIG. 1 is a schematic view of an arrangement for irradiating a surface with a number of radiation sources, a reflector and an optical system.

Corresponding parts are provided with the same reference numerals in all figures.

Figure 2:
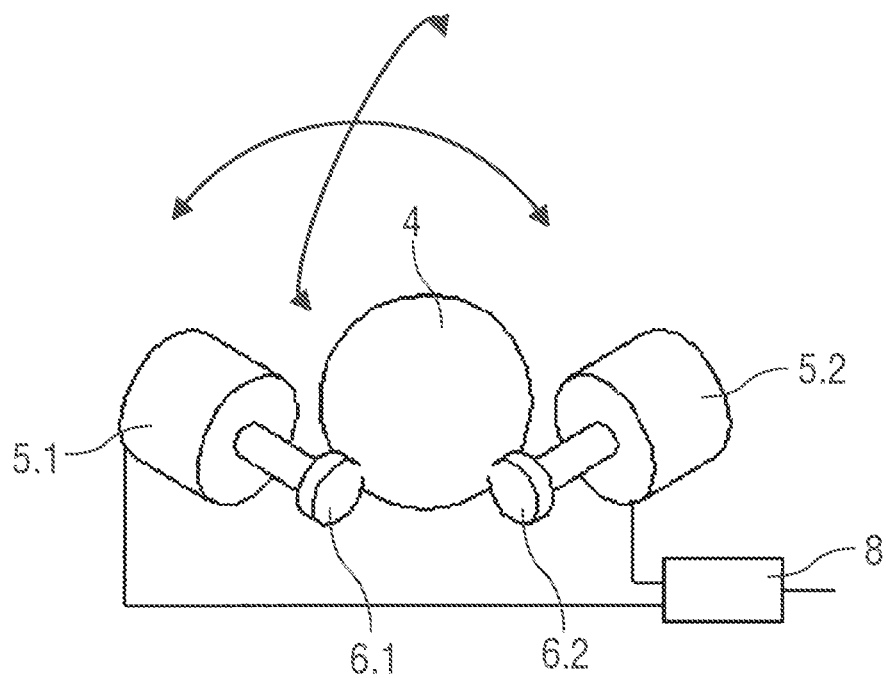
FIG. 2 shows schematic views of the reflector having a drive.
Figure 2:
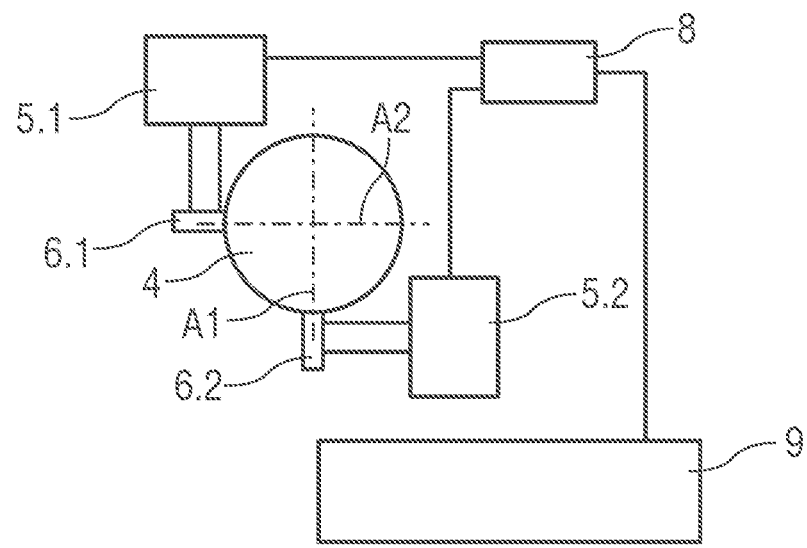

FIG. 1 is a schematic view of an arrangement 1 for irradiating a surface 2 for sterilizing this surface. FIG. 2 shows further schematic views of the arrangement 1. The arrangement comprises one or several radiation sources 3, for example LEDs and/or mercury vapour lamps, which are designed to emit ultraviolet radiation, in particular UV-C radiation. A reflector 4 is arranged for directed radiation of the ultraviolet radiation. The reflector 4 can have, in particular on its outer side, a circular cross-section and in particular be formed as a spherical section or semi-sphere. One or more, in particular two, drives 5.1, 5.2 can be provided for the alignment of the reflector 4. The drives 5.1, 5.2 each have an electric motor which engages the reflector 4 by means of positive or frictional locking. By way of example, each drive 5.1, 5.2 can have a friction wheel 6.1, 6.2 which abuts an outer surface of the reflector 4, in particular in such a way that the reflector 4 is rotatable about a first axis A1 by means of one of the drives 5.1, and in such a way that the reflector 4 is rotatable about a second axis A2 by means of the other of the drives 5.2, the second axis A2 being oriented at a right angle to the first axis A1.

An optical system 7 can be provided in the beam path emerging from the reflector 4 to further direct the radiation. The optical system 7 can comprise, for example, a scattering lens 7.1 and a converging lens 7.2 downstream of the scattering lens 7.1 in the beam path.

The drives 5.1, 5.2 can be connected to a drive control unit 8, which in turn can be connected to a control device 9.

Figure 3:
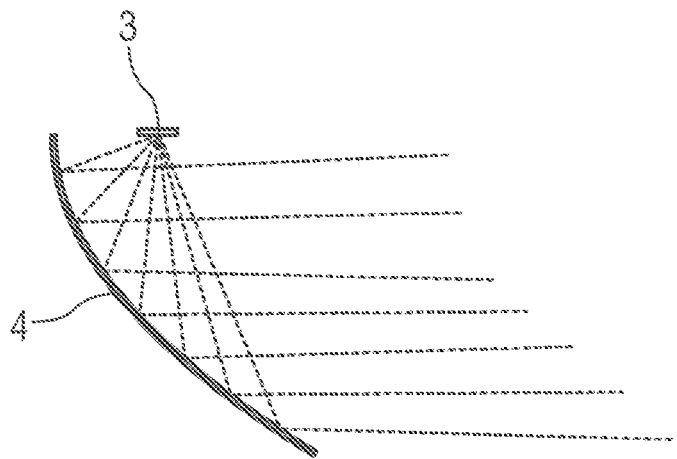
FIG. 3 is a schematic view of a reflector for distributing the radiation of a radiation source as uniformly as possible on the surface to be irradiated.

FIG. 3 shows a schematic view of an inner side of a reflector 4, which is designed to distribute the radiation of a radiation source 3 as uniformly as possible on the surface 2 to be irradiated. The inner side of the reflector 4 can, for example, be formed as an elliptical paraboloid. By means of the reflector 4 formed in this way, a radiometric output on the surface 2 to be irradiated can be optimized. The effective range of the radiation is thereby largely limited to this surface 2 and the available radiation power of the radiation source 3 is distributed largely uniformly over the surface 2.

Figure 4:
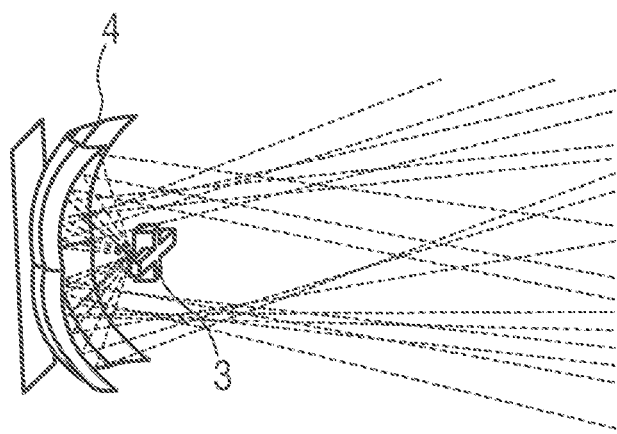
FIG. 4 is a schematic view of a reflector for concentrating the radiation of a radiation source on a small area of the surface to be irradiated.

FIG. 4 shows a schematic view of an inner side of a reflector 4 for concentrating radiation from a radiation source 3 on a small area of the surface 2 to be irradiated. The inner side of the reflector 4 can, for example, be designed as a free-form reflector comprising two or more hollow shapes which focus at least a large part of the radiation on a common focal point. By means of the reflector 4 formed in this way, a radiometric power can be focused on a small surface area 2 to be irradiated.

Figure 5:
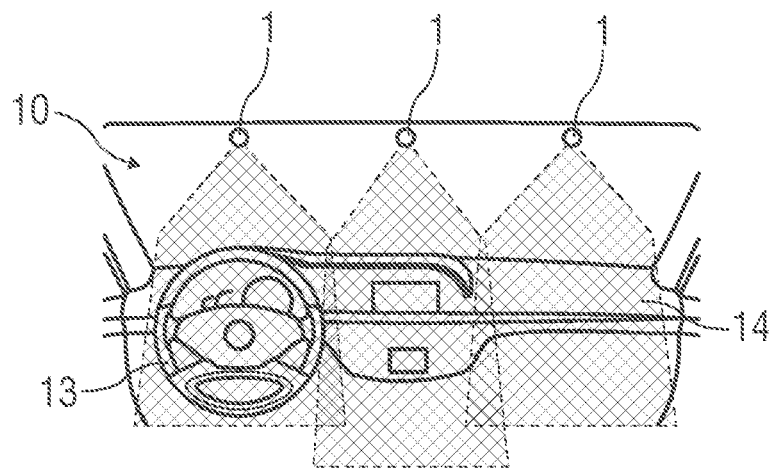
FIG. 5 is a schematic view of a vehicle interior having multiple reflectors.
Figure 6:
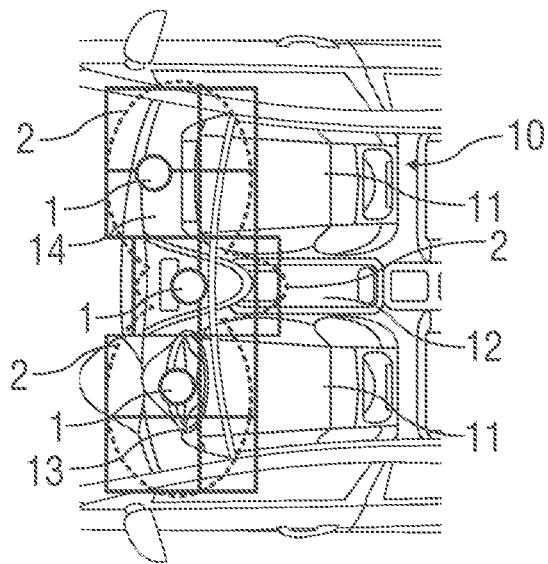
FIG. 6 is a schematic view of the vehicle interior having multiple reflectors.

FIGS. 5 and 6 show schematic views of a vehicle interior 10 having several arrangements 1, which can be formed as in FIGS. 1 to 3 and whose reflectors 4 can be formed as in FIG. 3 or 4. The arrangements 1 can be formed in a roof area of a vehicle and can be formed with or without an optical system 7. The reflectors 4 are formed in particular for distributing the radiation from a radiation source 3 as uniformly as possible over the surfaces 2 to be irradiated. The surfaces 2 to be irradiated are in particular at least parts of the vehicle seats 11, in particular front seats, as well as at least parts of a center console 12 and/or a dashboard on which operating elements can be provided, for example levers and switches, buttons or touch screens. Furthermore, a steering wheel 13 of the vehicle can be part of the surface 2 to be irradiated.

Figure 7:
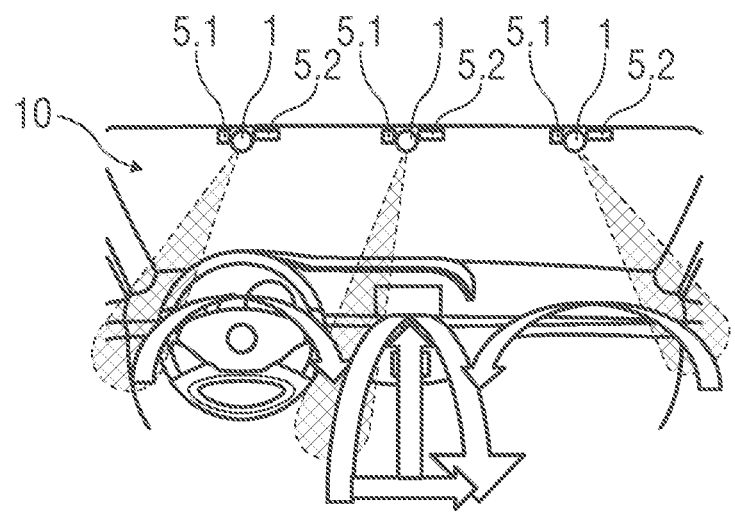
FIG. 7 is a schematic view of a vehicle interior having multiple reflectors and drives.
Figure 8:
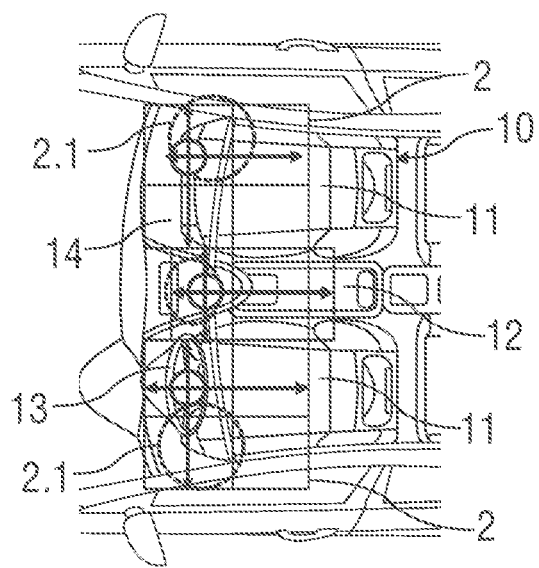
FIG. 8 is a schematic view of the vehicle interior having multiple reflectors and drives.

FIGS. 7 and 8 show schematic views of a vehicle interior 10 having several arrangements 1, which can be formed as in FIGS. 1 to 3 and whose reflectors 4 can be formed as in FIG. 3 or 4. The arrangements 1 can be formed in a roof area of a vehicle and can be formed with or without drives 5.1, 5.2 and with or without an optical system 7. In particular, the reflectors 4 are designed to concentrate the radiation from a radiation source 3 onto a small area 2.1 of the surface 2 to be irradiated.

The surfaces 2 to be irradiated are in particular at least parts of vehicle seats 11, in particular front seats, as well as at least parts of a center console 12 and/or a dashboard 14, on which operating elements can be provided, for example levers and switches, buttons or touchscreens. Furthermore, a steering wheel 13 of the vehicle can be part of the surface 2 to be irradiated.

By means of the drives 5.1, 5.2, the small area of the surface 2 to be irradiated can be displaced, for example in such a way that a larger surface area is traversed in a grid-like manner. By means of the control device 9, the areas can be traversed in such a way that all relevant areas are irradiated with a lethal dose sufficient for germs in biofilms, in particular pathogenic germs, such as viruses, bacteria or fungi.

Figure 9:
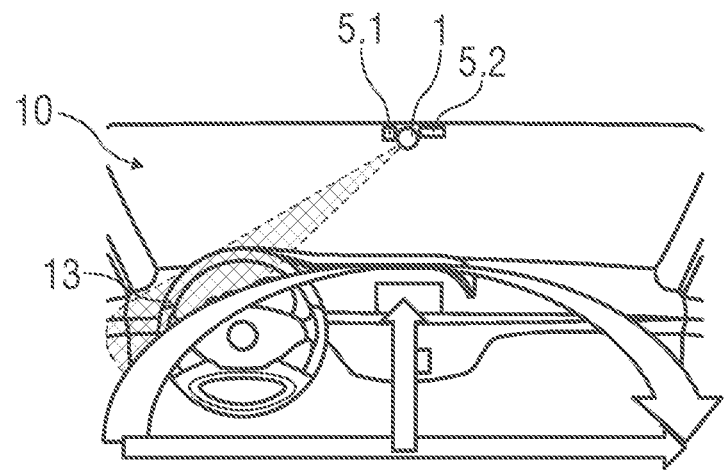
FIG. 9 is a schematic view of a vehicle interior having a reflector and drives.
Figure 10:
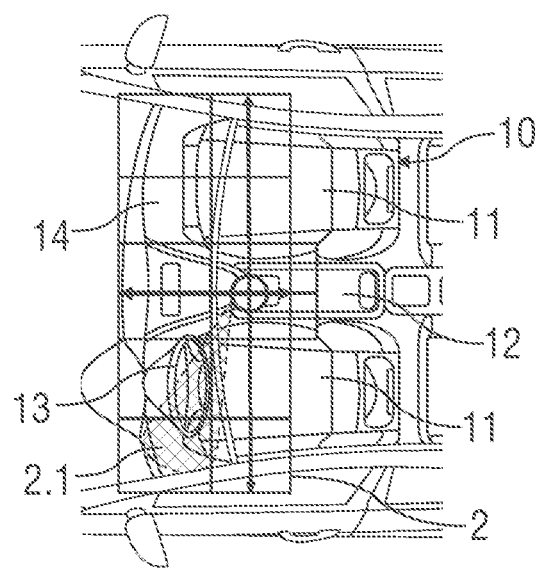
FIG. 10 is a schematic view of the vehicle interior having a reflector and drives.

FIGS. 9 and 10 show schematic views of a vehicle interior 10 having an arrangement 1, which can be designed as in FIGS. 1 to 3 and whose reflector 4 can be designed as in FIG. 3 or 4. The arrangement 1 can be formed in a roof area of a vehicle and can be formed with or without drives 5.1, 5.2 and with or without an optical system 7. In particular, the reflector 4 is designed to concentrate the radiation from a radiation source 3 onto a small area 2.1 of the surface 2 to be irradiated.

The surfaces 2 to be irradiated are in particular at least parts of vehicle seats 11, in particular front seats, as well as at least parts of a center console 12 and/or a dashboard 14, on which control elements can be provided, for example levers and switches, buttons or touch screens. Furthermore, a steering wheel 13 of the vehicle can be part of the surface 2 to be irradiated.

By means of the drives 5.1, 5.2, the small area 2.1 of the surface 2 to be irradiated can be shifted, for example in such a way that a larger surface 2 is traversed in a grid-like manner. By means of the control device 9, the surface areas can be traversed in such a way that all relevant areas are irradiated with a lethal dose sufficient for germs in biofilms, in particular pathogenic germs such as viruses, bacteria or fungi. In this case, the control device 9 can be used to adapt the duration of exposure to the radiation to the reduced radiation power resulting from the increased distance between the reflector 4 and the surface 2 to be irradiated.

Figure 11:
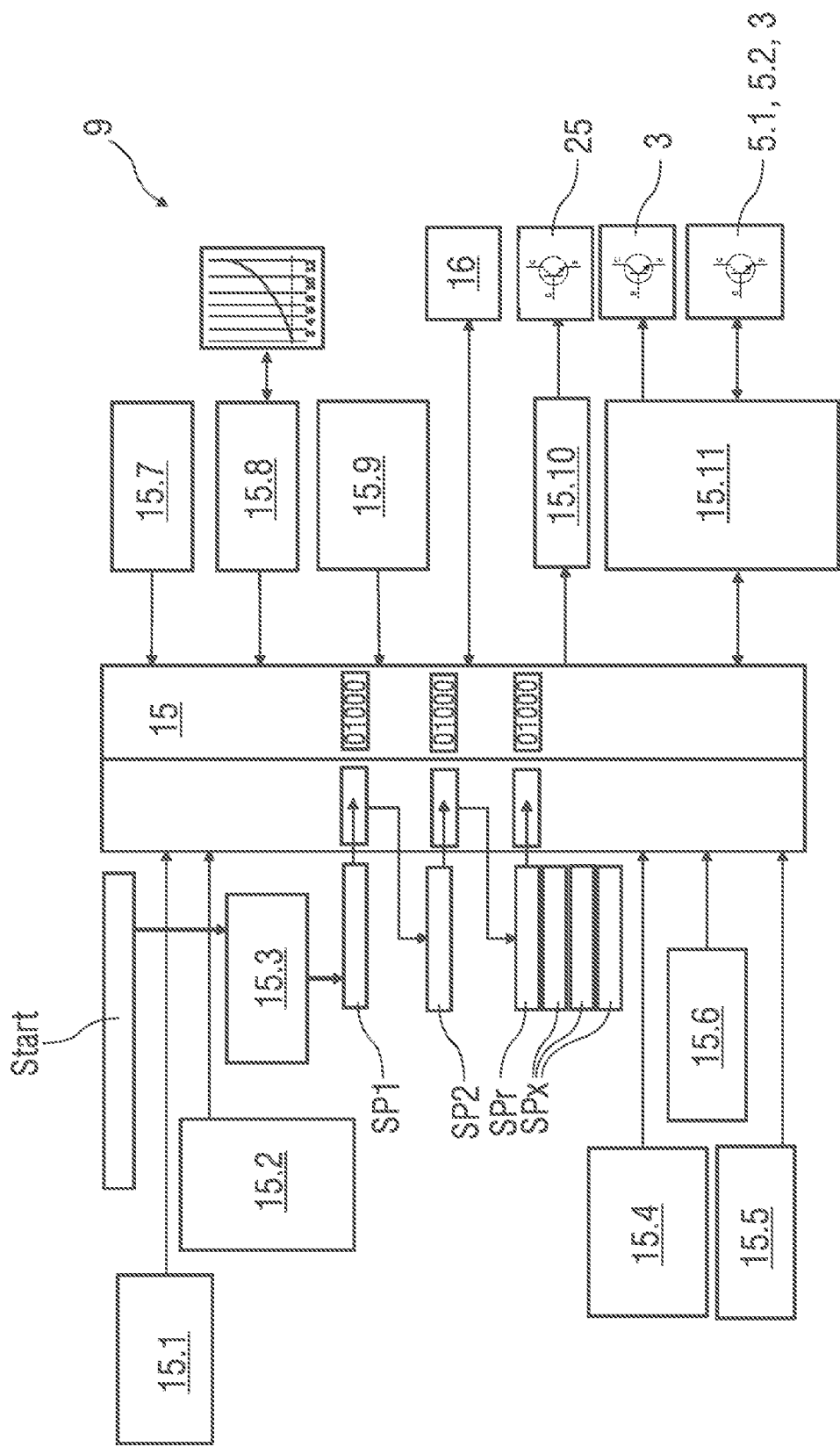
FIG. 11 is a schematic view of a control device for controlling the arrangement.

FIG. 11 shows a schematic view of the control device 9 for controlling the at least one arrangement 1. The control device 9 has, for example, a microcontroller 15 that can have a number of modules 15.1 to 15.11, in particular software modules, for example a module 15.1 for detecting empty journeys and idle times, a module 15.2 for detecting a connection of the vehicle 16 to a charging device, a module 15.3 for starting the sterilization and predetermining at least one start position SP1, SP2, SPx of each of the arrangements 1, a module 15.4 for stopping the sterilization for the purpose of occupant protection, a module 15.5 for detecting a battery state, a module 15.6 for calculating a required irradiation dose at a given distance from the radiation source 3, a module 15.7 for detecting a passenger throughput and/or seat occupancies, a module 15.8 for predicting an expected contamination at a given passenger throughput, a module 15.9 for determining the date, time and/or time of year, a module 15.10 for displaying a hygiene status in the vehicle 16 or for displaying a currently running sterilization on a display unit 25, and a module 15.11 for determining and/or setting start positions and/or target positions and/or actual positions of the arrangements 1 and for switching on and off the radiation sources 3.

The efficiency of the radiation can be increased by generating a vacuum or negative pressure in the empty vehicle interior 10, as this reduces extinction and absorption of the radiation and removes suspended matter. By thus using the ultraviolet radiation more effectively, hygiene is improved and interior materials are protected by reducing the irradiation to a necessary minimum.

By means of module 15.4, the vehicle interior 10 can be monitored to ensure that no living organism is present in the vehicle interior 10 during irradiation and/or evacuation. Furthermore, emergency stop devices can be provided to terminate the evacuation and/or to ventilate the vehicle interior 10.

FIG. 12 shows a schematic view of a system 17 for evacuating the vehicle interior 10. The system 17 comprises an actuator 18 for actuating a forced ventilation, an actuator 19 for actuating a forced ventilation, a vehicle computer 20, a sensor system 21 for interior monitoring and detection of living organisms, in particular persons, in the vehicle interior 10, for example by means of infrared and/or ultrasonic detectors. The actuators 18 and 19 can be designed as controlling elements and/or electromotive flaps. The vehicle computer 20 detects whether the vehicle 16 is open or closed and whether living beings are present in the vehicle. The vehicle computer 20 can control a heating, ventilation and air conditioning system 24 provided in the vehicle 16.

Furthermore, the system 17 comprises one or more emergency stop buttons 22 for terminating or interrupting the evacuation and/or for opening the actuators 18 and/or 19 for forced ventilation. The door openers of the vehicle 16 can also be used as emergency stop buttons 22.

Furthermore, the system 17 comprises a vacuum pump 23. Alternatively to the vacuum pump, the evacuation can be performed by means of a fan of a heating, ventilation and air conditioning system 24, which is provided in the vehicle 16 anyway. Furthermore, at least one arrangement 1 and the control device 9 are included in the system, as described above.

The control can take place in such a way that sterilization occurs during empty journeys. In particular, the control can take place in such a way that only or in particular those areas are sterilized where a high number of touches occur and/or which can be easily contaminated. The control system can be designed to track which areas have already been sterilized. Based on radiation power and distance from the radiation source, an exposure duration can be calculated in such a way that sterilization is performed safely and terminated after sufficient exposure. Based on the detected person throughput, a prediction of the expected re-contamination can be made. Re-contamination can then occur, for example, during empty journeys.

Each of the modules 15.1 to 15.11 can work out a program part of the control, possibly incorporating the results of one or more of the other modules 15.1 to 15.11. These can conditionally or unconditionally be incorporated in the control system.

By way of example, the module 15.1 for detecting empty journeys and idle times can be connected to a vehicle computer, a person monitoring system, and/or door contacts to detect an empty journey, for example in autonomous driving vehicles, or idle times in general. The vehicle can, for example, communicate that it is an empty journey/idle time. The control device 9 can start sterilization, for example focusing on specific areas, depending on the prognosis for re-contamination.

The module 15.5 for detecting the battery status can receive information from the vehicle 16 or from a battery charger regarding the charging state of a battery, and from the module 15.8 regarding the expected contamination. By way of example, in the case of an empty journey and good charging state, sterilization can occur in accordance with the expected re-contamination. In the case of a poor charging state, sterilization can be omitted, in particular for empty journeys.

The module 15.9 for determining the date, time and/or time of year can receive information from the vehicle computer. On the basis of a time, a processing of the time portions for the doses can take place. Furthermore, a possible service time and/or a charge can be taken into account for electric vehicles. Based on the time of year, forecasts of re-contamination can be made, for example in months with an increased risk of colds.

The invention claimed is:
1. An arrangement for irradiating a surface, comprising:
a radiation source configured to emit ultraviolet radiation;
a reflector for directional radiation of the ultraviolet radiation onto the surface;
a control device, wherein a dose of the ultraviolet radiation required for sterilizing the surface and/or a dose already administered is settable and/or determinable by the control device; and
a first drive and a second drive, wherein each of the first drive and the second drive has a respective friction wheel which abuts an outer surface of the reflector such that the reflector is rotatable around a first axis by the first drive and is rotatable around a second axis by the second drive.

2. The arrangement according to claim 1, wherein the reflector has a spherical section or semi-sphere on an outer side of the reflector.

3. The arrangement according to claim 1, wherein the reflector is formed on an inner side of the reflector for distributing the ultraviolet radiation as uniformly as possible on the surface.

4. The arrangement according to claim 1, wherein an inner side of the reflector is configured as an elliptical paraboloid.

5. An arrangement for irradiating a surface, comprising:
a radiation source configured to emit ultraviolet radiation;
a reflector for directional radiation of the ultraviolet radiation onto the surface; and
a control device, wherein a dose of the ultraviolet radiation required for sterilizing the surface and/or a dose already administered is settable and/or determinable by the control device;
wherein the reflector is configured on an inner side for concentrating the ultraviolet radiation on an area of the surface;
wherein the inner side of the reflector is configured as a free-form reflector comprising two or more hollow forms which focus at least a major part of the ultraviolet radiation onto a common focal point.

6. The arrangement according to claim 1 further comprising an optical system for aligning the ultraviolet radiation disposed in a beam path of the ultraviolet radiation emerging from the reflector.

7. The arrangement according to claim 1, wherein, by the control device, a time period of an effect of the ultraviolet radiation is adaptable to a radiation power varying as a result of an alignment by the first drive and the second drive and a distance between the reflector and the surface.

8. The arrangement according to claim 7, wherein the control device is configured to traverse the surface in a grid-like manner such that all relevant areas are irradiated with a lethal dose sufficient for germs in biofilms.

9. An arrangement for irradiating a surface, comprising:
a radiation source configured to emit ultraviolet radiation;
a reflector for directional radiation of the ultraviolet radiation onto the surface; and
a control device, wherein a dose of the ultraviolet radiation required for sterilizing the surface and/or a dose already administered is settable and/or determinable by the control device;
wherein the control device is configured to store a dose already administered in an event of an interruption of radiation of the ultraviolet radiation and to continue the radiation after the interruption until an intended dose is reached.

10. A vehicle, comprising:
a vehicle interior; and
an arrangement for irradiating a surface in the vehicle interior, wherein the arrangement comprises:
a radiation source configured to emit ultraviolet radiation;

a reflector for directional radiation of the ultraviolet radiation onto the surface; and a control device, wherein a dose of the ultraviolet radiation required for sterilizing the surface and/or a dose already administered is settable and/or determinable by the control device;

wherein a negative pressure or a vacuum is generatable in the vehicle interior during operation of the arrangement.

11. A vehicle, comprising:

a vehicle interior;

an arrangement for irradiating a surface in the vehicle interior, wherein the arrangement comprises:

a radiation source configured to emit ultraviolet radiation;

a reflector for directional radiation of the ultraviolet radiation onto the surface; and a control device, wherein a dose of the ultraviolet radiation required for sterilizing the surface and/or a dose already administered is settable and/or determinable by the control device; and a living being detector and an emergency stop button, wherein the vehicle interior is ventilated when a living being is detected or the emergency stop button is actuated.

* * * * *